US00PP30544P3

(12) United States Plant Patent

Theuws et al.

(10) Patent No.: US PP30,544 P3
(45) Date of Patent: May 28, 2019

(54) *ASPARAGUS* PLANT NAMED 'AMADEUS'

(50) Latin Name: *Asparagus officinalis*
Varietal Denomination: Amadeus

(71) Applicant: Bejo Zaden BV, Warmenhuizen (NL)

(72) Inventors: Johannes Henricus Adrianus Theuws, Warmenhuizen (NL); Lambert Willem Johannes Arends, Warmenhuizen (NL)

(73) Assignee: Bejo Zaden BV, Warmenhuizen (NL)

( * ) Notice: Subject to any disclaimer, the term of this patent is extended or adjusted under 35 U.S.C. 154(b) by 0 days.

(21) Appl. No.: 15/732,432

(22) Filed: Nov. 10, 2017

(65) Prior Publication Data

US 2018/0263164 P1 Sep. 13, 2018

Related U.S. Application Data

(60) Provisional application No. 62/600,984, filed on Mar. 7, 2017.

(51) Int. Cl.
*A01H 5/04* (2018.01)
*A01H 6/12* (2018.01)

(52) U.S. Cl.
USPC ..... Plt./260
CPC ..... *A01H 6/12* (2018.05)

(58) Field of Classification Search
USPC ..... Plt./260
CPC ... A01H 5/04; A01H 5/06; A01H 5/12; A01H 5/025; A01H 6/12; A01H 6/56
See application file for complete search history.

*Primary Examiner* — June Hwu
(74) *Attorney, Agent, or Firm* — The Webb Law Firm

(57) ABSTRACT

A new and distinct male variety of *asparagus* plant with high branching and uniform spears.

3 Drawing Sheets

Botanical classification: *Asparagus officinalis.*
Varietal denomination: 'Amadeus'.

BACKGROUND OF THE INVENTION

The present invention comprises a new and distinct *asparagus* plant known by the varietal name 'Amadeus'. The new variety is the result of a planned breeding program conducted by the inventors in 2007 in The Netherlands. The purpose of the breeding program was to develop 100% male hybrid *asparagus* varieties suitable for green harvesting in particular warm or cool climate types that exhibit good disease tolerance and a desirable eating quality. 'Amadeus' is the result of the crossing of an *Asparagus officinalis* variety referred to by the applicant as 08009 (female parent, unpatented) with an *Asparagus officinalis* variety referred to by the applicant as 08011 (male parent, unpatented). The first act of asexual reproduction of 'Amadeus' was conducted in 2010 by crown division in The Netherlands. 'Amadeus' has been trial and field tested and has been found to retain its distinctive characteristics and remain true to type through successive propagations. The present invention has not been evaluated under all possible environmental conditions. The phenotype may vary with variations in environment without a change in the genotype of the plant.

'Amadeus' is a high-branching fern, similar to its female parent. However, 'Amadeus' exhibits a more uniform spear size than both of its parental varieties.

When compared to *asparagus* variety named 'Grande' (unpatented), 'Amadeus' is similar to 'Grande' in having green spears (stalks) with some anthocyanin coloration on their bracts and tips at the stage of harvesting. However, 'Amadeus' exhibits smaller spears and taller stems than 'Grande'. Further, 'Amadeus' only produces male flowers, while 'Grande' produces both male and female flowers.

When compared to *asparagus* variety named 'UC157' (unpatented), 'Amadeus' exhibits spears that are more uniform in size than 'UC157'. Further, 'Amadeus' exhibits taller stems with higher branching ferns than 'UC157'. Additionally, 'Amadeus' only produces male flowers, while 'UC157' produces both male and female flowers.

Generally, when compared to other *asparagus* varieties known to the applicant, 'Amadeus' exhibits a very uniform spear size for harvesting. 'Amadeus' is also distinguishable from other varieties in the fact that it is 100% male. Additionally, 'Amadeus' exhibits good field tolerance, as well as tolerance against *asparagus* root rot (*Fusarium oxysporum*). Further, the spears of 'Amadeus' are tender, with good eating and keeping qualities.

DESCRIPTION OF THE DRAWINGS

The accompanying photographic drawings taken at approximately one year of age illustrate the new variety, with the color being as nearly true as is possible with color illustrations of this type.

DESCRIPTION OF THE PLANT

Figure 1:
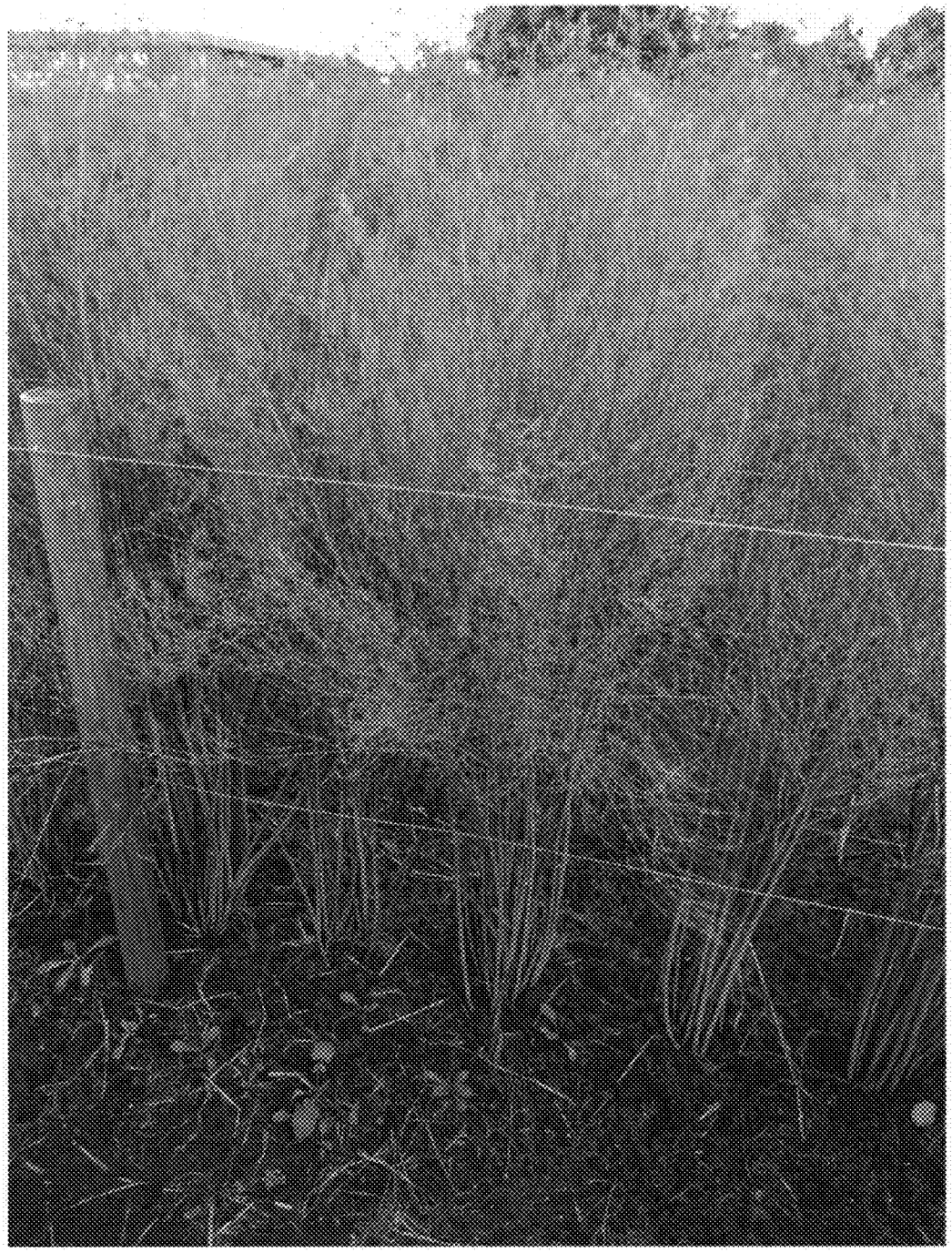
FIG. 1 shows a shows a view of multiple plants of the new variety.
Figure 2:
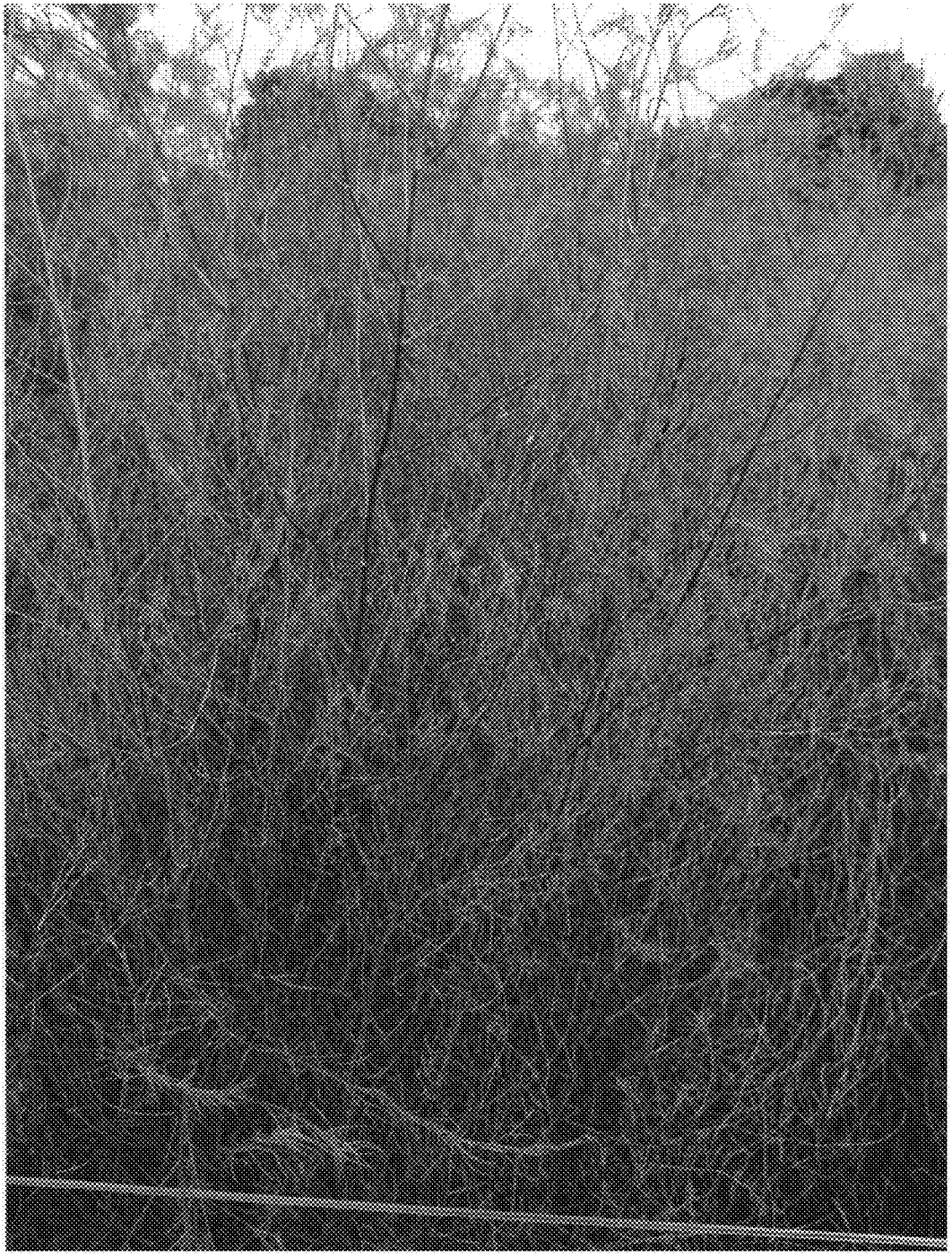
FIG. 2 shows a view of multiple plants of the new variety.
Figure 3:
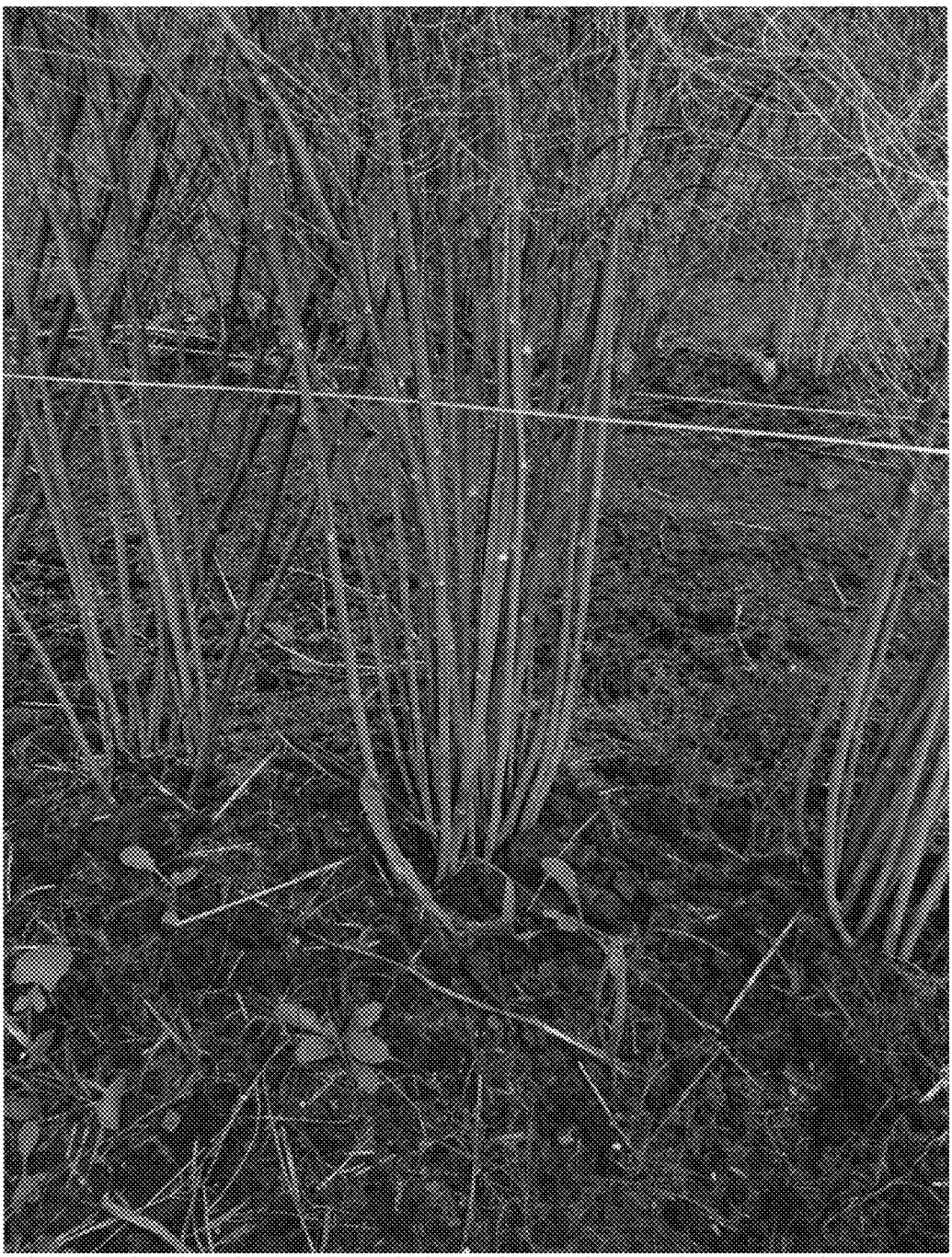
FIG. 3 shows close-up view of a plant of the new variety.

The following detailed description sets forth the characteristics of the new variety. Plants of the new variety were soil grown in the Netherlands under open field conditions under natural light. The emergence of spears occurs fairly early from planting when compared to other *asparagus* varieties known to the applicant and is dependent upon temperature and planting depth. The color readings and measurements were taken outdoors in the Netherlands under natural light on approximately one year old plants. Color references are primarily to The 2015 R.H.S. Colour Chart of The Royal Horticultural Society of London, Sixth Edition.

Stalks:

*Number of branches.*—50.

*Typical and observed branch color.*—Approximately 139A.

*Number of nodes below the first branch.*—12.

*Distance from the crown to the first branch.*—68 cm.

*Number of cladophyll nodes between the first and last branch.*—39.

*Distance between the first and last branch.*—130 cm.

*Number of cladophyll nodes beyond the last branch.*—20.

*Number of centimeters beyond the last branch.*—10.2 cm.

*Internode length between branches.*—4.6 cm.

*Internode length beyond the last branch.*—5.5 cm.

*Average number of stalks.*—11.

*Largest stalk diameter.*—15 mm.

*Mean diameter of three largest stalks, wherein the average spear diameter at the base of the apex and the middle of the spear are equal.*—15 mm.

*Length of highest headed stalk.*—198 cm.

*Color of stalk below the first branch, bloom removed.*—Between 139A and 140B.

*Color of stalk between the first and last branch, bloom removed.*—Between 139A and 140B.

*Color of stalk beyond the last branch, bloom removed.*—Between 139A and 140B.

*Anthocyanin coloration.*—Present at spear apex.

*Spear apex shape.*—Medium triangular.

*Average length of first bracts at base of spear apex.*—Short to medium.

*Average width of first bracts at base of spear apex.*—Small to medium.

*Opening of spear bracts.*—Weakly open.

*Attitude of spear bracts.*—Adpressed.

Flowers:

*Flowers.*—Length: 6 mm. Width at midpoint: 3.5 mm. Number of flowers per cluster (flowering node): 14. Longevity on the plant: Medium. Average time from planting to beginning of flowering (when at least 30% of plants have one flower open): Dependent on temperature when the crowns are planted, but generally about three weeks after spear emergence.

*Petals.*—Not applicable, only tepals are present.

*Tepals.*—Number of whorls: 1. Number of tepals per whorl: 6. Colors: Lower (abaxial) base: Approximately 59A. Lower (abaxial) tip: Approximately 139D. Lower (abaxial) midrib: Approximately 59A and 139A are both present. Lower (abaxial) margins: Approximately 139D. Upper (adaxial) base: Approximately 59A. Upper (adaxial) tip: Approximately 139D. Upper (adaxial) midrib: Approximately 59A and 139A are both present. Upper (adaxial) margins: Approximately 139D. Outer tepal length: 6 mm. Outer tepal width: 2 mm. Inner tepal length: 6 mm. Inner tepal width: 2 mm. Midrib of outer tepals, width: 0.6 mm. Midrib of inner tepals, width: 0.5 mm.

*Flower stalk peduncles.*—Length: 23 cm. Diameter: 1 mm. Color: Approximately 139A.

*Flower stalk pedicels.*—Length: 7 mm. Diameter: 0.2 mm. Color: Approximately 59A.

Fruit: Not applicable, as 'Amadeus' is a male variety and no fruit is developed.

Cladophylls:

*Average number per node.*—3 to 4.

*Length.*—9 mm.

*Width.*—0.3 mm.

*Shape.*—Overall: Acicular. Apex: Pointed. Base: Pointed.

*Margin type.*—Entire.

*Color.*—Between 144A and 144B.

Leaves: Not applicable, only cladophylls are present.

Reproduction organs:

*Gynoecium.*—Not applicable, as 'Amadeus' is a male variety.

*Androecium.*—

*Stamens.*—Number: 6. Length: 3 mm.

*Anthers.*—Length: 0.6 mm. Color: 17A. Pollen: Color: 17A. Amount: Minimal.

*Filaments.*—Length: 2.4 mm. Color: Approximately 155C.

General:

*Use.*—Fresh market green *asparagus.*

*Shipping quality of spears.*—Good.

*Storage life.*—Spears last up to 15 days, depending on storage conditions.

*Spear productivity.*—185 g/plant, based on a plant density of 25,000 plants/hectare in full season production.

*Temperature tolerance.*—Intermediate (Mediterranean) climate is preferable. Plants need cooler temperatures to go into dormancy and can withstand winter frost conditions when dormant.

I claim:

1. A new and distinct variety of *asparagus* plant, as is herein illustrated and described.

* * * * *